(12) United States Patent
Bocquenet et al.

(10) Patent No.: US 7,453,012 B2
(45) Date of Patent: Nov. 18, 2008

(54) CONTINUOUS PROCESS FOR THE HYDROGENATION OF NITRILES OR NITRO COMPOUNDS TO AMINES

(75) Inventors: Gérald Bocquenet, Communay (FR); André Chesnais, Saint-Symphorien (FR); Jean-Michel Desire, Villeurbanne (FR); Philippe Leconte, Meyzieu (FR); Lionel Sever, Luzinay (FR)

(73) Assignee: Rhodia Polyamide Intermediates, Saint_Fons (FR)

( * ) Notice: Subject to any disclaimer, the term of this patent is extended or adjusted under 35 U.S.C. 154(b) by 550 days.

(21) Appl. No.: 10/502,179

(22) PCT Filed: Jan. 20, 2003

(86) PCT No.: PCT/FR03/00161

§ 371 (c)(1),
(2), (4) Date: Apr. 18, 2005

(87) PCT Pub. No.: WO03/062188

PCT Pub. Date: Jul. 31, 2003

(65) Prior Publication Data

US 2007/0118001 A1    May 24, 2007

(30) Foreign Application Priority Data

Jan. 21, 2002  (FR) .................................. 02 00703

(51) Int. Cl.
*C07C 209/32* (2006.01)
*C07C 209/48* (2006.01)

(52) U.S. Cl. ..................... 564/492; 564/490; 564/491; 564/493; 564/494; 564/495

(58) Field of Classification Search ................... None
See application file for complete search history.

(56) References Cited

U.S. PATENT DOCUMENTS

| | | | | |
|---|---|---|---|---|
| 6,080,372 A | * | 6/2000 | Machado | .................... 422/190 |
| 6,232,488 B1 | * | 5/2001 | Boschat et al. | .............. 558/459 |
| 6,478,968 B1 | | 11/2002 | Perrona et al. | |
| 6,518,449 B1 | | 2/2003 | Boschat et al. | |

OTHER PUBLICATIONS

International Search Report corresponding to PCT/FR 2003/00161, issued Jul. 30, 2003, 4 pages.

* cited by examiner

*Primary Examiner*—Brian J Davis
(74) *Attorney, Agent, or Firm*—Buchanan, Ingersoll & Rooney, PC

(57) ABSTRACT

A process for the hydrogenation of compounds comprising nitrile or nitro functional groups to amine, aminonitrile or aminonitro compounds is provided. The process can be a continuous process conducted in the presence of a heterogeneous hydrogenation catalyst in divided form and a basic compound. The reaction can be conducted in a stirred reactor comprising an external loop for circulating the reaction mixture, allowing one portion of the hydrogenated products to be separated without withdrawing the catalyst, by using tangential filtration. The process may be especially useful in the hydrogenation of adiponitrile to an aminocapronitrile/hexamethylenediamine mixture.

18 Claims, 2 Drawing Sheets

US 7,453,012 B2

CONTINUOUS PROCESS FOR THE HYDROGENATION OF NITRILES OR NITRO COMPOUNDS TO AMINES

This application is an application under 35 U.S.C. Section 371 of International Application No. PCT/FR03/00161 filed on Jan. 20, 2003.

The present invention relates to a process for the hydrogenation of compounds comprising nitrile or nitro functional groups to amine, aminonitrile or aminonitro compounds.

It relates more particularly to a continuous process of hydrogenation.

Hydrogenation of dinitriles to the corresponding diamines is a process which has been used for a long time, in particular the hydrogenation of adiponitrile to hexamethylenediamine, one of the base materials in the preparation of nylon-6,6.

There has been an increasing interest in recent years in the hydrogenation (also sometimes known as semihydrogenation) of aliphatic dinitriles to aminonitriles, in particular the hydrogenation of adiponitrile to 6-aminocapronitrile, resulting either directly, or via caprolactam, in nylon-6.

Thus, U.S. Pat. No. A-5,151,543 discloses a process for the selective hydrogenation of aliphatic dinitriles to the corresponding aminonitriles, at 25-150° C. and under a pressure of greater than atmospheric pressure, in the presence of a solvent in a molar excess of at least 2/1 with respect to the dinitrile, the solvent comprising liquid ammonia or an alcohol with 1 to 4 carbon atoms and an inorganic base which is soluble in the said alcohol, in the presence of a Raney catalyst, the aminonitrile obtained being recovered as main product.

Patent WO-A-93/16034 discloses a process for the preparation of 6-aminocapronitrile by hydrogenation of adiponitrile in the presence of an inorganic base, of a transition metal complex, the transition metal being of low valency and chosen from chromium, tungsten, cobalt and iron, and of Raney nickel as catalyst, under hydrogen pressure and at a temperature of 50° C. to 90° C.

Patent WO-A-96/18603 discloses the semihydrogenation of aliphatic dinitriles to aminonitriles by hydrogen in the presence of a catalyst based on optionally doped Raney cobalt or nickel and of a strong inorganic base, the starting hydrogenation medium comprising water, aminonitrile and/or diamine which are capable of being formed and unconverted dinitrile.

All these hydrogenation processes result in the aminonitrile and are presented as being able to be employed continuously in an industrial plant.

However, to obtain an economic process compatible with industrial operation, it is necessary to be able to recycle the unconverted reactant and to consume as little catalyst as possible per kilogram of compounds produced.

A process has already been proposed, in French Patent 2 749 191, which allows a portion of the hydrogenated products to be drawn off from the reaction mixture without withdrawing catalyst, by carrying out tangential filtration in the presence of gaseous hydrogen in order to prevent the catalyst from being deactivated.

However, that document does not disclose a process that can also continuously regenerate the catalyst in order to allow completely continuous operation of the process.

It is one of the objects of the present invention to provide a hydrogenation process allowing continuous operation with recycling and regeneration of the catalyst. Such a process allows the hydrogenation to take place with a high selectivity and with a high yield and to be carried out on an industrial scale.

For this purpose, the invention provides a continuous process for the hydrogenation of compounds comprising nitrile or nitro functional groups to amine or aminonitrile compounds in the presence of a heterogeneous hydrogenation catalyst in divided form and of a basic compound, characterized in that it consists in:

feeding, into a stirred reactor:
    a first stream, of reactant to be hydrogenated,
    a second stream, of catalyst,
    a third stream, of basic compound and
    a fourth stream, of hydrogen in order to maintain the reactor under a pressure of hydrogen;

withdrawing, from the reactor, at least a fifth stream consisting of the reaction mixture and including hydrogen bubbles dispersed in the said mixture;

making this fifth stream circulate in at least one loop, which runs into the bottom and the top of the reactor, and removing, by heat exchange with the said fifth stream, the heat produced by the hydrogenation reaction so as to maintain the reaction mixture at a temperature below 150° C.;

withdrawing, from this fifth stream circulating in one of the loops, a sixth stream containing a portion of the hydrogenate separated from the catalyst; and withdrawing, from the reactor or from one of the circulation loops, a seventh stream, of hydrogenate which is fed into a liquid/solid separation step, and recovering the liquid phase containing the catalyst-free hydrogenate and the solid phase formed by the catalyst, the said solid phase being treated in order to be regenerated before being recycled into the second, catalyst stream.

The process of the invention comprises the circulation of the reaction mixture outside the reactor, making it possible, on the one hand, for the heat generated by the reaction to be removed in a controlled and simple manner and, on the other hand, for the hydrogenate to be withdrawn without disturbing the catalyst concentration in the reaction mixture and without deactivating it. Finally, the process of the invention allows the catalyst to be continuously replaced with a mixture of fresh catalyst and regenerated catalyst.

The term "hydrogenate" refers in the present text to the liquid phase of the reaction mixture leaving the reactor. This hydrogenate comprises the hydrogenated compounds and the reactants that have not been converted, together with the solvents if they are present.

According to an advantageous feature of the invention, a heat exchanger is present in one of the reaction mixture circulation loops. When this heat exchanger is placed in the loop comprising the withdrawal of the sixth, hydrogenate stream, called for the sake of clarity the first circulation loop, this exchanger is located downstream of the said point of withdrawal of the sixth, hydrogenate stream with respect to the direction of flow of the reaction mixture. This heat exchange makes it possible to remove the heat generated by the hydrogenation reaction and to maintain the reaction mixture at a defined temperature. Such a temperature control is important as it allows the desired selectivity to be obtained, especially in the case of partial hydrogenation of dinitriles to aminonitriles.

This operation of controlling the temperature or removing the heat may be carried out, in a second method of implementing the process of the invention, by placing a heat exchanger in a second reaction mixture circulation loop, in which second loop an eighth stream, of the said reaction mixture withdrawn from the bottom of the reactor and recycled after cooling into the said reactor, flows. In this method of implementation, the first circulation loop advantageously does not include a heat exchanger, thus making it possible to reduce the overall residence time of the reaction mixture in each circulation loop and thus limiting catalyst deactivation. This is because the catalyst contained in a mixture containing nitrile compounds with a low hydrogen concentration rapidly becomes deactivated. Since the hydrogenation reaction continues in the circulation loop, the hydrogenation concentration rapidly decreases. An advantage of the process of the invention is that it allows a very short reaction mixture circulation time in the loops, and therefore makes it possible to minimize the residence time of the catalyst and to maintain, in all the reaction mixture circulation loops, a three-phase mixture comprising the catalyst in solid form, the hydrogenate in liquid form and dispersed hydrogen bubbles.

The hydrogenate is withdrawn, according to the process of the invention, in the first reaction mixture circulation loop. This withdrawal is carried out through a filter medium in order in this way to maintain all the catalyst in the circulation reaction mixture. As filter medium, it is possible to use any type of material resistant to the pressure of the reaction mixture, to the temperature conditions and to any chemical attack.

In a preferred method of implementation, and for allowing a withdrawal without increasing the residence time of the reaction mixture in the circulation loop, this withdrawal is advantageously carried out with tangential-type filtration. Advantageously, the filter medium is formed by a porous medium placed tangentially to the direction of flow of the fifth stream in the first circulation loop. An example of tangential filtration suitable for the invention is that disclosed in French Patent No. 2 749 191.

As porous media suitable for the invention, mention may be made of metal frit media, carbon media or media consisting of an inorganic or organic membrane placed over a flat or tubular support. The said membrane, called the active layer, has a thickness of a few microns, for example between 5 µm and 100 µm.

Metal media, which have better chemical and heat resistance, are preferred. As an example, these media are made, for example, of stainless steel.

Moreover, these porous media may be easily maintained and cleaned. Thus, it is possible to regenerate the filter medium after a certain period of use, by washing with various solutions, such as water, acids or bases.

Preferably, the removal of hydrogenate represents from 0.1% to 10% by volume of the flow of reaction mixture circulating in the first loop.

Advantageously, to prevent the catalyst from being entrained in the sixth, hydrogenate stream, the porous medium has pores of between 1 nanometre and 10 microns in diameter.

According to a preferred feature, especially in the case of partial hydrogenation of compounds to aminonitrile or aminonitro products, the filtration step is carried out in the presence of hydrogen in gas form, the reaction mixture being saturated with dissolved hydrogen. This gaseous hydrogen may advantageously come from the gas bubbles dispersed in the reaction mixture by the stirring present in the reactor. It is also possible to provide a hydrogen feed in the circulation loops in order to maintain the presence of hydrogen in gas form in all the loops.

The process of the invention therefore makes it possible to withdraw the hydrogenate representing the production of the process without extracting the catalyst from the reaction mixture and above all under conditions that prevent deactivation of the catalyst. This aspect is especially important when the reaction mixture contains compounds with nitrile or nitro functional groups that have not yet been hydrogenated.

According to one other feature of the invention, the process comprises a step for withdrawing a portion of the catalyst in order to allow it to be treated, so as to be regenerated before it is recycled in the hydrogenation process. Thus, a portion of the reaction mixture is continuously or periodically withdrawn, either from one of the reaction mixture circulation loops or directly by withdrawal from the reactor, in order to form a seventh stream. This seventh stream, comprising hydrogenate and catalyst, is treated in a solid/liquid separation step. Any liquid/solid separation process may be used, such as filtration, centrifuging or settling. The catalyst thus separated is advantageously washed with water, preferably slightly basic water (advantageously with a pH of greater than 9), in order to recover the hydrogenate. The washing water is thus advantageously added to the separated liquid phase. This mixture also represents a production of hydrogenate and may be added to the sixth stream recovered in the tangential filtration step.

The hydrogenate may be used as such in other synthesis processes or may be purified, for example by distillation. Thus, the various products contained in the hydrogenate may be separated by distillation in several columns connected in series.

The catalyst recovered is advantageously subjected to a regeneration treatment before being recycled into the second, catalyst stream fed into the reactor.

The catalyst is regenerated using known processes, especially by the process described in Patent Application FR 2 773 086. The process consists, in the case of a Raney type catalyst, either in treating the catalyst with a basic solution in order to dissolve at least some of the aluminate compounds formed or in hydrogenating the catalyst in basic medium. In general, the regeneration processes comprise a washing step in order to remove the compounds that have built up on the catalyst and optionally a reduction step, for example using hydrogen.

As indicated above, the catalyst may be recovered either from one of the reaction mixture circulation loops or by direct withdrawal from the reactor.

The process of the invention therefore makes it possible simultaneously to recover the hydrogenate and to recycle the regenerated catalyst without disturbing the operation of the reactor and without inducing or generating rapid deactivation of the catalyst present in the reaction mixture.

The process of the invention applies to the complete or partial hydrogenation of compounds comprising nitrile or nitro functional groups. It applies more particularly to a process for the partial hydrogenation or semihydrogenation of compounds comprising nitrile or polynitrile functional groups.

This process is advantageously used for hydrogenating adiponitrile to aminocapronitrile and hexamethylenediamine. The aminocapronitrile may be used to manufacture ε-caprolactam or in a polymerization process for the manufacture of polyamides.

The nitrile compounds suitable for the invention are especially aliphatic dinitrile compounds.

The aliphatic dinitriles which can be employed in the process of the invention are thus more particularly the dinitriles of general formula (I):

$$NC-R-CN \qquad (I)$$

in which R represents a linear or branched alkylene or alkenylene group having from 1 to 12 carbon atoms.

In the process of the invention, use is preferably made of dinitriles of formula (I) in which R represents a linear or branched alkylene radical having from 2 to 6 carbon atoms.

Mention may in particular be made, as examples of such dinitriles, of adiponitrile, methylglutaronitrile, ethylsuccinonitrile, malononitrile, succinonitrile, glutaronitrile and their mixtures, in particularly mixtures of adiponitrile and/or of methylglutaronitrile and/or of ethylsuccinonitrile which can originate from the same process for the synthesis of adiponitrile.

In practice, the case where $R=(CH_2)_4$ will be the most frequent as this corresponds to the use of adiponitrile (ADN) in the present process.

According to one particularly advantageous method of implementing the present invention, the compounds to be hydrogenated are aromatic compounds comprising at least one nitro functional group.

Preferably, the said compounds have at least two nitro functional groups and at least one $C_6$-$C_{14}$, preferably $C_8$-$C_{10}$, aromatic unit, which may or may not be substituted with one more saturated or unsaturated, linear, cyclic or branched $C_1$-$C_{10}$ hydrocarbon radicals and/or one or more hydroxyl radicals.

More specifically, the aforementioned hydrocarbon radicals, possibly substituting the said aromatic units, may be chosen from $C_1$-$C_{10}$, preferably $C_1$-$C_6$, alkyl, aryl, alkylaryl and arylalkyl radicals.

As aromatic unit, mention may especially be made of benzene and naphthalene rings, which may or may not be substituted with one or more methyl, ethyl, propyl, butyl, pentyl or hexyl radicals and/or isomers thereof.

The process according to the invention may be implemented using at least one compound from mononitrobenzene, mononitrotoluene, dinitrotoluene, paranitrocumene and orthonitrophenol.

In the case of the hydrogenation of dinitrile compounds, the mean composition of the reaction mixture is determined according to the desired degree of conversion and the desired degree of selectivity.

Thus, the reaction mixture advantageously comprises an amount of water less than or equal to 20%. Preferably, the water content is between 1.5% and 7% with respect to all of the liquid constituents of the mixture.

However, this process may be carried out in the absence of water, but in the presence either of liquid ammonia or of aliphatic alcohols.

In general, the hydrogenation process is carried out in the presence of a solvent, which may correspond to one of the products obtained by hydrogenation. Thus, in the case of the hydrogenation of adiponitrile, the solvent is advantageously hexamethylenediamine.

The catalysts used in this semihydrogenation process can be a Raney nickel or a Raney cobalt comprising, in addition to the nickel or the cobalt and the residual amounts of the metal removed from the starting alloy during the preparation of the catalyst, that is to say generally aluminium, one or more other elements, often known as dopants, such as, for example, chromium, titanium, molybdenum, copper, tungsten, iron, zinc, rhodium or iridium. Among these dopants, chromium, copper, titanium, iron, rhodium, iridium and their mixtures are regarded as the most advantageous. These dopants usually represent, by weight with respect to the weight of nickel or of cobalt, from 0% to 15% and preferably from 0% to 10%.

Use may also advantageously be made of a catalyst based on ruthenium or on rhodium deposited on a support. This catalyst can also comprise metal dopants included in the list mentioned for the Raney metals.

The amount of catalyst employed can vary very widely depending in particular on the nature of the catalyst or the reaction conditions chosen. By way of indication, use may be made of 0.5% to 20% by weight of catalyst with respect to the total weight of the reaction mixture, and generally of 1% to 12% by weight.

The second catalyst stream comprising the regenerated catalyst and the fresh catalyst is advantageously conditioned before being introduced into the hydrogenation reactor. This conditioning is especially described in French Patent 2 806 081. This process consists in adding the catalyst to a solvent and then adding to this mixture the amount of base needed to condition the catalyst. The solvent is chosen to be a poor solvent for the basic compound, thus making it possible to fix, for example by adsorption, molecules of basic compounds, generally strong mineral bases, on the surface of the catalyst.

The strong mineral bases suitable for the invention are alkali metal or alkaline-earth metal hydroxides, for example LiOH, NaOH, KOH, RbOH, CsOH, tetraalkylammonium hydroxides, such as tetraethylammonium or tetramethylammonium hydroxide, and mixtures thereof.

The hydrogenation process of the invention is generally carried out at a reaction temperature of less than or equal to 150° C., preferably less than or equal to 120° C. and even more preferably less than or equal to 100° C.

Specifically, this temperature is between ambient temperature (approximately 20° C.) and 100° C.

Prior to, simultaneously with or subsequent to the heating, the reaction chamber is brought to the appropriate hydrogen pressure, that is to say, in practice, between 1 bar (0.10 MPa) and 100 bar (10 MPa) and preferably between 5 bar (0.5 MPa) and 50 bar (5 MPa).

The other conditions which govern the hydrogenation process in accordance with the invention relate to conventional technical arrangements known per se.

Furthermore, these conditions can be modified in order to modify the degree of conversion of the dinitrile to diamines according to whether a high selectivity for aminonitrile is desired or conversely complete hydrogenation of the dinitriles is desired.

According to another preferred feature of the invention, the liquid medium for maintaining the Raney metal is preferably water. The aluminium concentration in the Raney metal is preferably between 2 and 6%. A low aluminium content in the catalyst is preferable as it makes it possible to vary the selectivity of the reaction and to reduce the phenomenon of clogging in the porous media.

According to another feature of the invention, the amount of strong base added in the step for conditioning the catalyst is between 0.1 mol and 50 mol per kg of catalyst. The optimum amount of base is determined for each catalyst.

According to a preferred method of implementing the invention, the strong base is added in the conditioning step in the form of a concentrated solution or in pure form.

Moreover, the amount of solvent added depends on the degree of solubility of the water in this solvent and on the desired level of concentration in the phase containing the strong base. Advantageously, the ratio by weight of the solvent to the water will be at least equal to 1, preferably greater than or equal to 2.

According to the invention, the solvent is chosen from compounds which have an affinity (solubility, for example) with water or the liquid for preserving the Raney metal and which, on the contrary, have no affinity (low solubility) with the strong mineral base. What is meant by insolubility of the strong base in the solvent, or more specifically in the liquid phase formed by the solvent and the water or the preservation liquid, is a low solubility for the base, for example less than 1% by weight.

In a preferred method of implementing the invention, the solvent is advantageously an amine, preferably an amine corresponding to that obtained by the hydrogenation reaction, or liquid ammonia if the hydrogenation were carried out in a liquid ammonium medium. This is because, advantageously, the choice of solvent must allow further products to not be introduced into the hydrogenation mixture and therefore allow separation processes and possibly recycling processes to be carried out easily and inexpensively, and therefore with little penalty for the process as regards the technical and economic standpoint.

An additional amount of basic compound may be added to the reaction mixture in the form of a separate stream or as a mixture with the water stream or solvent stream. This additional amount of base is intended to saturate the reaction mixture with basic compounds in order not to change the amount of base deposited on the catalyst.

BRIEF DESCRIPTION OF THE DRAWINGS

Further details and advantages of the invention will become more clearly apparent in the light of the detailed description of a method of implementing the invention, given solely by way of illustration and with reference to the appended figures in which.

Figure 1:
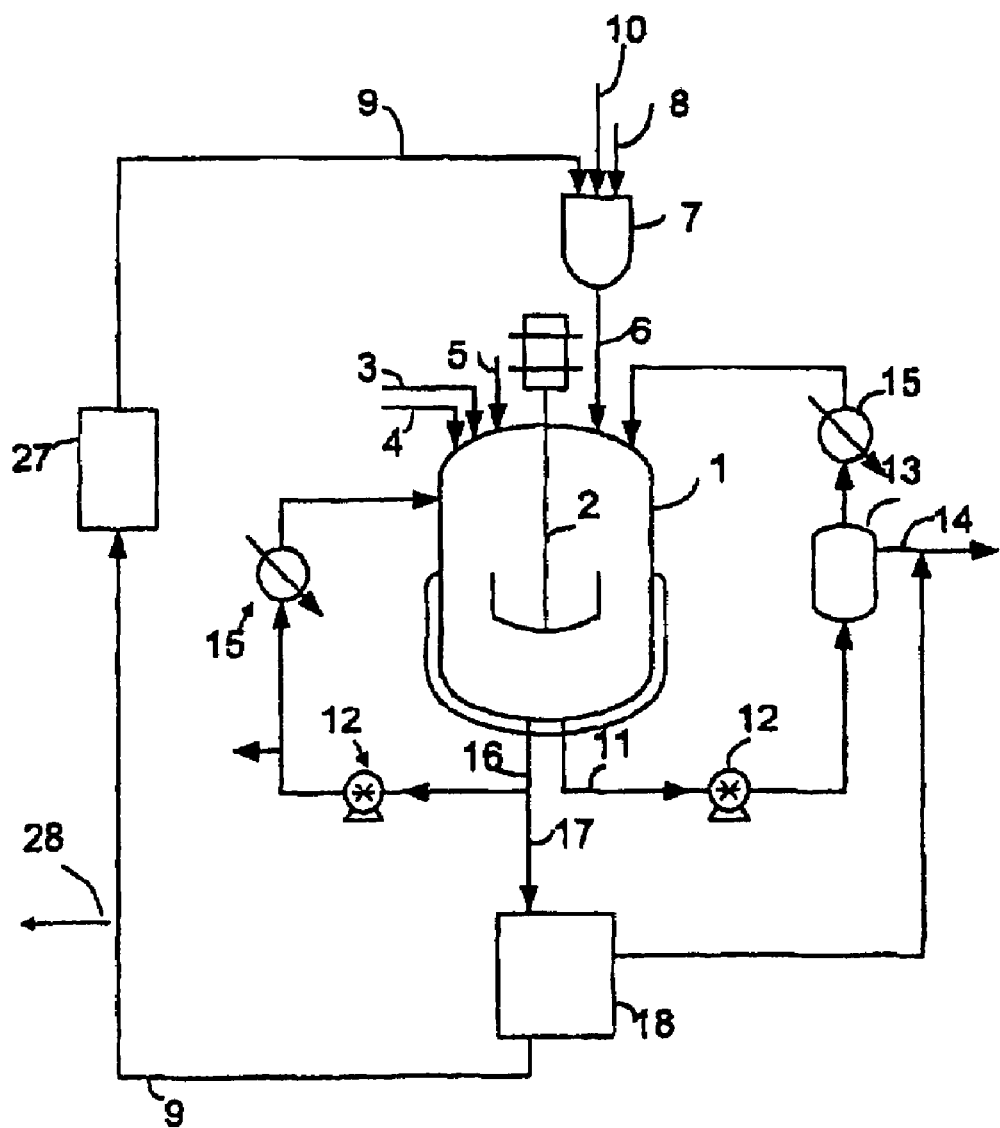
FIG. 1 shows a schematic diagram of the process of the invention.

The process of the invention is carried out in a hydrogenation reactor 1 which includes a stirrer 2 for keeping the solid in suspension in the reaction mixture and to disperse the gas (hydrogen) forming the overhead of the reactor in the form of bubbles. The stirrer may, for example, be a self-suction stirrer of the cavitator type, of the Rushton type or of the multiblade type, the blades advantageously being inclined.

This stirring makes it possible to obtain a three-phase mixture comprising a solid phase consisting of the catalyst, a liquid phase consisting mainly of the various organic compounds to be hydrogenated or that have been hydrogenated, and a gas phase consisting of the hydrogen bubbles dispersed in the reaction mixture.

The reactor may include a double-walled jacket for controlling the temperature by using a heat-transfer fluid.

The reactor 1 includes a first line 3 for feeding the reactant to be hydrogenated, forming the first stream. In the example illustrated, this reactant is adiponitrile, advantageously dissolved in a solvent such as hexamethylenediamine. It includes a second line 4 for feeding basic compounds, advantageously in aqueous solution, forming the third stream, for example an aqueous potassium hydroxide solution.

In the method of implementation illustrated, the hydrogenation is carried out in the presence of an amount of water of between 1.5% and 7% by weight of the liquid mass of the reaction mixture, this water advantageously being fed in the form of solvent for the basic compounds. However, the process of the invention may be carried out in the absence of water and in the presence of other solvents, such as ammonia and aliphatic alcohols, such as methanol, ethanol or propanol. In the latter case, the basic compounds are added in the form of alcoholic solutions.

The reactor 1 also includes a line 5 for feeding hydrogen gas, constituting the fourth stream and forming the reactor overhead.

The catalyst is introduced into the reactor via the line 6 in the form of a suspension in a solvent prepared in a conditioning tank 7. This suspension forms the second stream.

In the method of implementation illustrated, this catalyst suspension is obtained by introducing, into the tank 7, a solvent such as hexamethylenediamine via the line 8 and the recycled catalyst, after having been optionally regenerated, via the line 9. The fresh catalyst and a solution of basic compounds, for example an aqueous potassium hydroxide solution, are also introduced via the line 10.

According to the invention, the reaction mixture is withdrawn at the bottom of the reactor 1 via a line 11, which forms a first circulation loop, and is fed back into the top of the reactor 1. This circulation loop includes a pump 12 compatible for circulating a three-phase mixture. The reaction mixture is fed into a tangential filter 13 shown schematically. In this filter 13, a portion of the liquid phase is filtered through the porous medium, formed by a metal mesh made of steel with a pore diameter of less than 10 microns, and withdrawn via the line 14.

In the method of implementation illustrated, the loop 11 also includes a heat exchanger 15 placed after the tangential filter 13, allowing the reaction mixture to be cooled to a defined temperature in order to maintain the temperature in the reactor within the abovementioned desired range.

At the bottom of the reactor 1, there is a second withdrawal 16 of the reaction mixture, forming a second circulation loop. A portion of the reaction mixture circulating in this loop 16 is taken off via the line 17 and fed into a solid/liquid separation device 18. This second circulation loop may also include a pump 12 and a heat exchanger 15.

Figure 2:
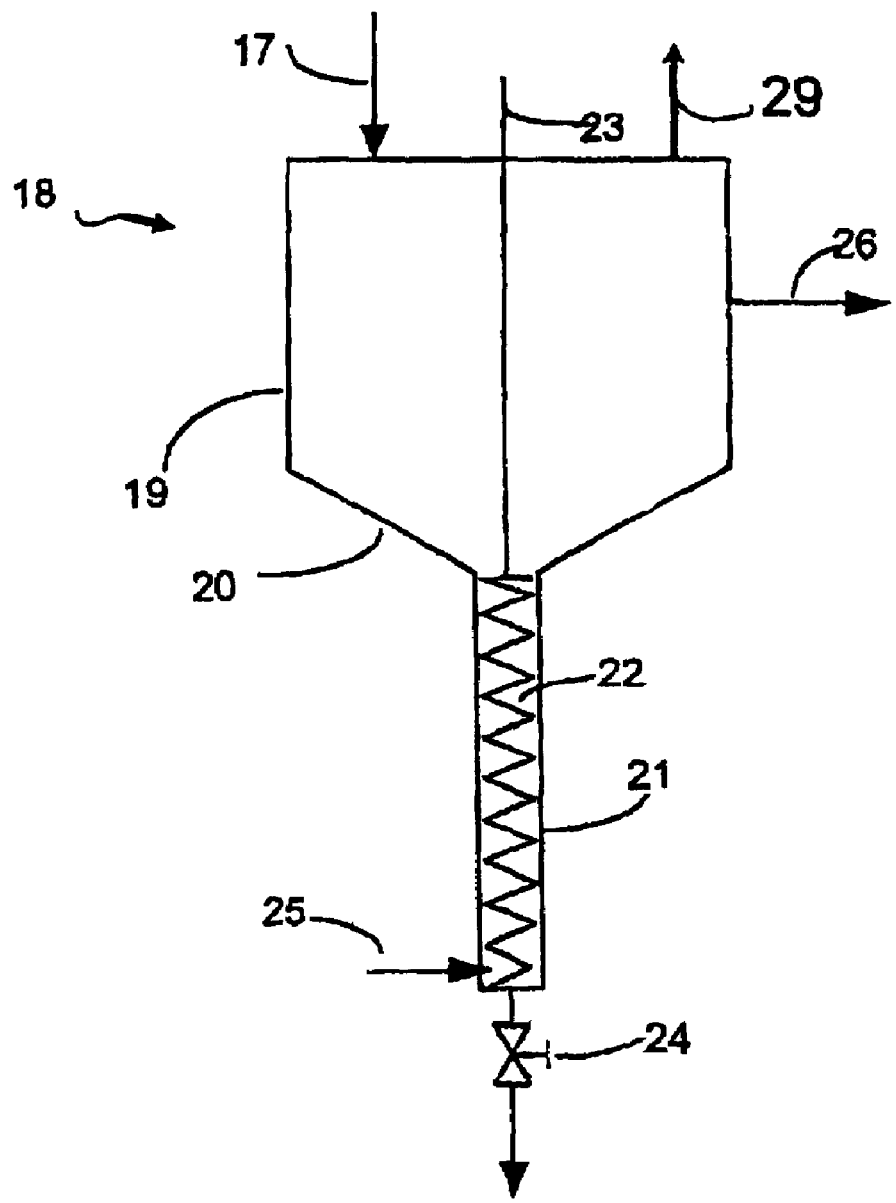
FIG. 2 shows a schematic diagram of the solid/liquid separation device.

One particular embodiment of the device 18 is illustrated in FIG. 2.

This device 18 has an upper portion 19 comprising a lower portion 20 of conical shape. The end of the cone 20 is extended by a pipe 21 of small cross section, in which is placed a means 22 for keeping the solid that builds up in the said pipe moving. This means 22 is, for example, a feed screw driven in movement by the shaft 23 and a motor (not illustrated). The pipe 21 at its lower end has a valve 24 for withdrawing the solid present. A line 25 runs into the pipe 21, advantageously at its lower portion, in order to feed in slightly basic water for washing the catalyst present in the said pipe 21. The reaction mixture withdrawn via the line 17 is fed into the upper portion 19 of the device 18 via a valve (not illustrated) or into an intermediate tank used as a lock (also not illustrated) and the supernatant liquid phase is withdrawn via a line 26, either as production of the hydrogenation process or in order to be mixed with the hydrogenate withdrawn via the line 14 through the filter 13. The device also includes an outlet 29 for discharging the gases coming from the reaction mixture.

This embodiment described above is given merely by way of indication. Other liquid/solid separation devices may be employed without departing from the scope of the invention.

In the embodiment illustrated, the catalyst recovered at the outlet of the pipe 21 via the valve 24 is recycled via the line 9 into the catalyst conditioning tank 7. Advantageously, before it is introduced into the tank 7, the catalyst is regenerated in a unit illustrated schematically at 27. This unit may comprise a reactor for treating the catalyst with hydrogen in basic medium. This unit may also include a washer for washing the catalyst, for example with a basic solution.

The line 9 advantageously includes a tap-off 28 for removing a portion of the spent catalyst.

The plant described above has been given merely as an illustration. Thus, the arrangement of the heat exchanger, the catalyst withdrawal and the number of reaction mixture circulation loops may be different without departing from the scope of the invention.

The invention claimed is:

1. A continuous process for the hydrogenation of compounds comprising nitrile or nitro functional groups to amine or aminonitrile compounds in the presence of a heterogeneous hydrogenation catalyst in divided form and of a basic compound said process comprising the steps of:
   a) feeding, into a stirred reactor:
   a first stream, of reactant to be hydrogenated,
   a second stream, of catalyst,
   a third stream, of basic compound, and
   a fourth stream, of hydrogen in order to maintain the reactor under a pressure of hydrogen;
   b) withdrawing, from the reactor, at least a fifth stream consisting of the reaction mixture and including hydrogen bubbles dispersed in the said mixture;
   c) making this fifth stream circulate in at least one loop, which runs into the bottom and the top of the reactor, and removing, by heat exchange with the said fifth stream, the heat produced by the hydrogenation reaction so as to maintain the reaction mixture at a temperature below 150° C.;
   d) withdrawing, from this fifth stream circulating in one of the loops, a sixth stream containing a portion of the hydrogenate separated from the catalyst;
   e) withdrawing, from the reactor or from one of the circulation loops, a seventh
   stream, of hydrogenate which is fed into a liquid/solid separation step, and
   f) recovering the liquid phase containing the catalyst-free hydrogenate and the solid phase formed by the catalyst, the said solid phase being treated in order to be regenerated before being recycled into the second catalyst stream.

2. The process according to claim 1, wherein the heat is removed by a heat exchanger placed downstream of the said withdrawal of the sixth stream of hydrogenated compounds in the circulation loop for the said fifth stream.

3. The process according to claim 1, just after step e), further comprising the step of:
   e) withdrawing an eighth stream of the reaction mixture from the reactor and said stream being circulated in a second loop before being recycled into the reactor, the heat being removed by a heat exchanger placed in the said circulation loop for said eighth stream.

4. The process according to claim 1, wherein the sixth stream is withdrawn through a filter medium.

5. The process according to claim 4, wherein the filter medium is a porous medium placed tangentially to the direction of the fifth stream circulating in the loop.

6. The process according to claim 5, wherein the porous medium is made of metal.

7. The process according to claim 5, wherein the filter medium comprises a membrane placed on a support.

8. The process according to claim 1, wherein the reaction mixture further includes a solvent.

9. The process according to claim 1, wherein the reaction mixture further includes water, ammonia or an alcohol.

10. The process according to claim 9, wherein the reaction mixture comprises from 1.5% to 7% by weight of water with respect to the liquid mass of the reaction mixture.

11. The process according to claim 1, wherein in step e), the liquid/solid separation carried out on the seventh stream is a settling, filtering or centrifuging step.

12. The process according to claim 11, wherein the liquid/solid separation is carried out in a device comprising an upper portion having a bottom in the form of a cone, and a pipe of small cross section extending from the end of the cone, a means for moving the solid being placed in the pipe of small cross section, the reaction mixture being fed into the said upper portion, the liquid phase separated from the solid being withdrawn from the said upper portion, and the settled solid being recovered from the bottom of the pipe of small cross section.

13. The process according to claim 12, wherein water is added into the pipe of small cross section.

14. The process according to claim 1, wherein the regenerated catalyst obtained in step f) is fed into the second catalyst stream of step a).

15. The process according to claim 1, wherein the second catalyst stream of step a) consists of a mixture comprising the catalyst, a basic compound and optionally a solvent in which the basic compound is insoluble, with a basic compound/catalyst ratio being between 0.1 mol and 50 mol of basic compounds per 1 kg of catalyst.

16. The process according to claim 15, wherein the catalyst in the second catalyst stream is a mixture of fresh catalyst and regenerated catalyst.

17. The process according to claim 1, wherein the catalyst is a Raney nickel or a Raney cobalt comprising between 2% and 6% by weight of aluminum and optionally a dopant being chromium, titanium, molybdenum, copper, tungsten, iron, zinc, rhodium or iridium.

18. The process according to claim 1, wherein the compound being hydrogenated is adiponitrile.

* * * * *